US010426521B2

(12) United States Patent
Mosnier et al.

(10) Patent No.: US 10,426,521 B2
(45) Date of Patent: Oct. 1, 2019

(54) VERTEBRAL OSTEOSYNTHESIS EQUIPMENT

(71) Applicant: MEDICREA INTERNATIONAL, Rillieux la Pape (FR)

(72) Inventors: Thomas Mosnier, Rochetaillee sur Saone (FR); Frank Schwab, New York City, NY (US)

(73) Assignee: Medicrea International, Rillieux la Pape (FR)

( * ) Notice: Subject to any disclaimer, the term of this patent is extended or adjusted under 35 U.S.C. 154(b) by 80 days.

(21) Appl. No.: 15/568,605

(22) PCT Filed: Apr. 14, 2016

(86) PCT No.: PCT/IB2016/052125
§ 371 (c)(1),
(2) Date: Oct. 23, 2017

(87) PCT Pub. No.: WO2016/170452
PCT Pub. Date: Oct. 27, 2016

(65) Prior Publication Data

US 2018/0153588 A1 Jun. 7, 2018

(30) Foreign Application Priority Data

Apr. 24, 2015 (FR) ..................................... 15 53722

(51) Int. Cl.
*A61B 17/70* (2006.01)
*A61B 17/86* (2006.01)
*A61B 17/00* (2006.01)

(52) U.S. Cl.
CPC ...... *A61B 17/7037* (2013.01); *A61B 17/7032* (2013.01); *A61B 17/7035* (2013.01); *A61B 17/8685* (2013.01); *A61B 2017/00526* (2013.01)

(58) Field of Classification Search
CPC ........... A61B 17/7001; A61B 17/7032; A61B 17/7034; A61B 17/7035; A61B 17/7037;
(Continued)

(56) References Cited

U.S. PATENT DOCUMENTS 4,946,458 A * 8/1990 Harms ............... A61B 17/7002 606/264
5,628,740 A * 5/1997 Mullane ............. A61B 17/7037 606/307

(Continued)

FOREIGN PATENT DOCUMENTS

WO WO9855038 12/1998

*Primary Examiner* — Lynnsy M Summitt
(74) *Attorney, Agent, or Firm* — Defillo & Associates, Inc.; Evelyn A Defillo

(57) ABSTRACT

The equipment (1) includes at least one connecting bar and at least one anchor member (1) of the "tulip" type and of the so-called "polyaxial" type. According to the invention, the head (3) forms an articulation portion (15). The body (2) forms an articulation cavity (8) for receiving the articulation portion (15), defined by a bearing wall (9). The anchor member (1) includes a ring (20) bearing against said bearing wall (9). The ring (20) and a distal bearing surface of the head (3) includes inter-engagement means (16, 21) having, in a first angular position of the ring (20), a first inter-engagement position of the ring (20) in which play exists between the ring (20) and the bearing wall (9), and having, in a second angular position of the ring (20), a second inter-engagement position in which said play is eliminated such that the head (3) is made immobile, or substantially immobile, relative to the body (2).

10 Claims, 3 Drawing Sheets

(58) Field of Classification Search
CPC .............. A61B 17/7038; A61B 17/704; A61B 17/7041; A61B 17/7043; A61B 17/7046
See application file for complete search history.

(56) References Cited

U.S. PATENT DOCUMENTS

| | | | | | |
|---|---|---|---|---|---|
| 5,725,528 | A * | 3/1998 | Errico | A61B 17/7035 | 606/266 |
| 5,735,851 | A * | 4/1998 | Errico | A61B 17/7035 | 606/266 |
| 5,752,957 | A * | 5/1998 | Ralph | A61B 17/7037 | 606/266 |
| 5,800,435 | A * | 9/1998 | Errico | A61B 17/7007 | 606/261 |
| 6,050,997 | A * | 4/2000 | Mullane | A61B 17/7035 | 606/250 |
| 7,033,358 | B2 * | 4/2006 | Taylor | A61B 17/7037 | 606/277 |
| 7,163,538 | B2 * | 1/2007 | Altarac | A61B 17/7035 | 606/86 A |
| 7,163,539 | B2 * | 1/2007 | Abdelgany | A61B 17/7037 | 606/86 A |
| 7,207,992 | B2 * | 4/2007 | Ritland | A61B 17/7007 | 606/86 A |
| 7,572,280 | B2 * | 8/2009 | Dickinson | A61B 17/7007 | 606/266 |
| 7,731,734 | B2 * | 6/2010 | Clement | A61B 17/7035 | 606/246 |
| 7,744,635 | B2 * | 6/2010 | Sweeney | A61B 17/1671 | 606/264 |
| 7,763,054 | B2 * | 7/2010 | Clement | A61B 17/7037 | 606/265 |
| 7,819,902 | B2 * | 10/2010 | Abdelgany | A61B 17/7037 | 606/267 |
| 7,850,719 | B2 * | 12/2010 | Gournay | A61B 17/7037 | 606/278 |
| 7,862,594 | B2 * | 1/2011 | Abdelgany | A61B 17/7037 | 606/266 |
| 7,875,060 | B2 * | 1/2011 | Chin | A61B 17/7007 | 606/266 |
| 7,892,257 | B2 * | 2/2011 | Abdelgany | A61B 17/7037 | 606/246 |
| 7,927,359 | B2 * | 4/2011 | Trautwein | A61B 17/7035 | 606/264 |
| 8,002,807 | B2 * | 8/2011 | Abdelgany | A61B 17/7037 | 606/246 |
| 8,016,861 | B2 * | 9/2011 | Mitchell | A61B 17/7005 | 606/264 |
| 8,048,132 | B2 * | 11/2011 | Wu | A61B 17/7032 | 606/264 |
| 8,057,515 | B2 * | 11/2011 | Flynn | A61B 17/7035 | 606/246 |
| 8,066,746 | B2 * | 11/2011 | Glerum | A61B 17/7037 | 606/278 |
| 8,083,775 | B2 * | 12/2011 | Winslow | A61B 17/7005 | 606/264 |
| 8,092,503 | B2 * | 1/2012 | Felix | A61B 17/7058 | 606/264 |
| 8,097,020 | B2 * | 1/2012 | Markworth | A61B 17/7011 | 606/247 |
| 8,097,023 | B2 * | 1/2012 | Cline, Jr. | A61B 17/7037 | 606/264 |
| 8,097,024 | B2 * | 1/2012 | Winslow | A61B 17/7019 | 606/264 |
| 8,137,384 | B2 * | 3/2012 | Heiges | A61B 17/1655 | 606/254 |
| 8,162,990 | B2 * | 4/2012 | Potash | A61B 17/7032 | 606/266 |
| 8,192,470 | B2 * | 6/2012 | Biedermann | A61B 17/7034 | 606/265 |
| 8,211,155 | B2 * | 7/2012 | Winslow | A61B 17/7019 | 606/257 |
| 8,257,401 | B2 * | 9/2012 | Cermak | A61B 17/7037 | 606/267 |
| 8,292,934 | B2 * | 10/2012 | Justis | A61B 17/7037 | 606/264 |
| 8,308,772 | B2 * | 11/2012 | Clement | A61B 17/7037 | 606/267 |
| 8,333,792 | B2 * | 12/2012 | Winslow | A61B 17/7005 | 606/305 |
| 8,337,536 | B2 * | 12/2012 | Mitchell | A61B 17/7019 | 606/257 |
| 8,398,683 | B2 * | 3/2013 | Berrevoets | A61B 17/7032 | 606/267 |
| 8,409,256 | B2 * | 4/2013 | Arnold | A61B 17/7004 | 606/269 |
| 8,430,913 | B2 * | 4/2013 | James | A61B 17/7005 | 606/264 |
| 8,480,713 | B2 * | 7/2013 | Rezach | A61B 17/7041 | 606/246 |
| 8,491,639 | B2 * | 7/2013 | James | A61B 17/7037 | 606/267 |
| 8,506,609 | B2 * | 8/2013 | Biedermann | A61B 17/7037 | 606/266 |
| 8,585,741 | B2 * | 11/2013 | Gabelberger | A61B 17/7035 | 606/264 |
| 8,617,216 | B2 * | 12/2013 | Brumfield | A61B 17/7035 | 606/246 |
| 8,636,781 | B2 * | 1/2014 | Biedermann | A61B 17/7032 | 606/279 |
| 8,777,954 | B2 * | 7/2014 | McLean | A61B 17/7032 | 606/86 A |
| 8,940,032 | B2 * | 1/2015 | Harper | A61B 17/7041 | 606/328 |
| 9,017,390 | B2 * | 4/2015 | Biedermann | A61B 17/8605 | 606/305 |
| 9,101,405 | B2 * | 8/2015 | Dickinson | A61B 17/7055 | |
| 9,113,960 | B2 * | 8/2015 | Hansell | A61B 17/7035 | |
| 9,131,971 | B2 * | 9/2015 | Biedermann | A61B 17/8605 | |
| 9,144,441 | B2 * | 9/2015 | Biedermann | A61B 17/7076 | |
| 9,186,184 | B2 * | 11/2015 | Janowski | A61B 17/7038 | |
| 9,192,412 | B2 * | 11/2015 | Meyrat | A61B 17/7035 | |
| 9,198,693 | B2 * | 12/2015 | Rinehart | A61B 17/7035 | |
| 9,247,974 | B2 * | 2/2016 | Tornier | A61B 17/8605 | |
| 9,333,016 | B2 * | 5/2016 | Biedermann | A61B 17/844 | |
| 9,452,006 | B2 * | 9/2016 | Biedermann | A61B 17/844 | |
| 9,456,859 | B2 * | 10/2016 | Peukert | A61B 17/7037 | |
| 9,579,125 | B2 * | 2/2017 | Raju | A61B 17/8883 | |
| 9,649,137 | B2 * | 5/2017 | Rinner | A61B 17/7052 | |
| 9,801,664 | B2 * | 10/2017 | Hammer | A61B 17/7032 | |
| 9,855,078 | B2 * | 1/2018 | Faulhaber | A61B 17/7044 | |
| 9,861,388 | B2 * | 1/2018 | Biedermann | A61B 17/7002 | |
| 9,987,047 | B2 * | 6/2018 | Protopsaltis | A61B 17/7035 | |
| 10,098,669 | B2 * | 10/2018 | Byrnes | A61B 17/7037 | |
| 10,117,679 | B2 * | 11/2018 | Biyani | A61B 17/7037 | |
| 2004/0006342 | A1 * | 1/2004 | Altarac | A61B 17/7007 | 606/246 |
| 2007/0072493 | A1 * | 3/2007 | Sournac | A61B 17/7037 | 439/715 |
| 2007/0093832 | A1 | 4/2007 | Kbdelgany | | |
| 2007/0100339 | A1 * | 5/2007 | Clement | A61B 17/7037 | 606/277 |
| 2007/0173817 | A1 * | 7/2007 | Sournac | A61B 17/7037 | 606/250 |
| 2008/0021464 | A1 * | 1/2008 | Morin | A61B 17/7007 | 606/250 |
| 2008/0065073 | A1 * | 3/2008 | Perriello | A61B 17/7011 | 606/86 A |
| 2009/0118772 | A1 * | 5/2009 | Diederich | A61B 17/8685 | 606/301 |
| 2010/0036417 | A1 | 2/2010 | James | | |
| 2010/0036437 | A1 * | 2/2010 | Mitchell | A61B 17/7005 | 606/305 |
| 2010/0100137 | A1 | 4/2010 | Justis | | |
| 2010/0174322 | A1 * | 7/2010 | Abdelgany | A61B 17/7037 | 606/301 |
| 2011/0046684 | A1 * | 2/2011 | Abdelgany | A61B 17/7037 | 606/305 |
| 2011/0208248 | A1 | 8/2011 | Barrus | | |

(56) References Cited

U.S. PATENT DOCUMENTS

2012/0010658 A1* 1/2012 Kirschman ........ A61B 17/7044 606/246
2012/0035667 A1* 2/2012 Van Nortwick ... A61B 17/7035 606/305
2012/0083845 A1* 4/2012 Winslow ............ A61B 17/7007 606/264
2012/0095512 A1* 4/2012 Nihalani ............ A61B 17/7004 606/251
2012/0143257 A1* 6/2012 Winslow ............ A61B 17/7005 606/264
2012/0158065 A1* 6/2012 Jouve ................. A61B 17/7001 606/276
2012/0197309 A1* 8/2012 Steele ................ A61B 17/7085 606/301
2012/0221053 A1* 8/2012 Copf .................. A61B 17/7032 606/251
2012/0221055 A1* 8/2012 Copf .................. A61B 17/7041 606/264
2012/0290010 A1* 11/2012 Zamani .............. A61B 17/7035 606/264
2013/0253595 A1* 9/2013 Zucherman ........ A61B 17/8625 606/305
2014/0074169 A1* 3/2014 Shorez ............... A61B 17/7035 606/264
2014/0088650 A1* 3/2014 Taddia ............... A61B 17/7037 606/267
2015/0134006 A1* 5/2015 Ziolo ................. A61B 17/7032 606/278
2016/0058476 A1* 3/2016 Sournac ............. A61B 17/7032 606/267
2016/0287293 A1* 10/2016 Karas ................. A61B 17/7037
2017/0020574 A1* 1/2017 Biedermann ...... A61B 17/7037
2018/0036039 A1* 2/2018 Biedermann ...... A61B 17/7032
2018/0055542 A1* 3/2018 Biedermann ...... A61B 17/7037
2018/0055545 A1* 3/2018 Biedermann ...... A61B 17/7083
2018/0092670 A1* 4/2018 Crossgrove ........ A61B 17/7064
2018/0206896 A1* 7/2018 Yoon .................... A61B 17/863
2019/0038319 A1* 2/2019 Biedermann ...... A61B 17/7032

* cited by examiner

VERTEBRAL OSTEOSYNTHESIS EQUIPMENT

CROSS REFERENCE TO RELATED APPLICATION

This application is a national stage entry of PCT/IB2016/052125 filed Apr. 14, 2016, under the International Convention claiming priority over French Patent Application No. 1553722 filed Apr. 24, 2015.

BACKGROUND OF THE INVENTION

The present invention relates to a vertebral osteosynthesis equipment. It also relates to a method for manufacturing an anchor member comprised by this equipment.

To treat the degeneration of one or more vertebral joints, it is well known to use a vertebral osteosynthesis equipment comprising connecting bars intended to connect several vertebrae to be treated to one another and anchor members (pedicle screws and/or laminar hooks) making it possible to connect these bars to the vertebrae. As an example, patent application publication No. WO 98/55038 describes such an equipment.

The bars are curved according to the desired correction of the position of the vertebrae; if necessary, two adjacent anchor members connected to a same bar can be brought closer together or further apart before complete immobilization of the anchor members relative to the bar, to reduce a curvature of the spine in the frontal plane.

At least one anchor member can be of the so-called “tulip” type, i.e., comprising a wider head that forms an engagement duct of the connecting bar, the axis of this duct generally being secant to the axis of this head. This duct is closed, after placement of the connecting bar therein, by a threaded member screwed in the head. The body of the anchor member can be in the form of a threaded rod intended to be screwed in the resected pedicle of a vertebra or in the form of a hook intended to be inserted behind the lamina of a vertebra. The anchor member can be “monoaxial”, i.e., with said head secured to the body, or “polyaxial”, i.e., with said head articulated relative to said body. This articulation is in particular done by arranging a spherical part or sphere portion at the proximal end of said body and arranging, at the base of the head, in the bottom of said housing, a hole for the engagement of the body and a seat for articulated reception of said spherical part or sphere portion.

In practice, the anchor members are placed on the vertebrae, then the connecting bar(s) are curved depending on the repositioning of the vertebrae to be obtained, then these bars are placed in the different engagement ducts formed by the heads of the anchor members, and the threaded members are placed on these heads to retain the bars in said engagement duct; a movement of two adjacent anchor members connected to a same bar can be done at this stage, to bring the two vertebrae closer together or further apart on one side; once this corrections is done, the threaded members are tightened so as to immobilize the bars relative to said heads.

The monoaxial anchor members have the advantage of perfectly transmitting to the vertebrae the corrections imposed by the curvature of the bar(s) and the separating or approach corrections of two vertebrae; they have the major drawback, however, of making it difficult to engage a bar in the duct formed by the heads of the anchor members.

The advantages and drawbacks of the polyaxial anchor members are reversed: the engagement of a bar in the ducts formed by the heads of the anchor members is easy due to the articulation of these heads, but the transmission to the vertebrae of the corrections imposed by the curvature of the bar(s) and the separating or approach corrections of two vertebrae are done imperfectly, for this same reason of articulation of the heads.

It may be considered to use monoaxial anchor members and polyaxial anchor members on a same assembly, which nevertheless has the major drawback of making the placement of the equipment and the performance of corrections of the spinal column much more complex.

Patent application publications Nos. US 2010/036417 A1 and US 2007/093832 A1 describe pieces of equipment not making it possible to resolve the aforementioned drawbacks.

SUMMARY OF THE INVENTION

The present invention therefore precisely aims to provide vertebral osteosynthesis equipment resolving the aforementioned drawbacks, i.e., allowing for transmission to the vertebrae of the corrections required by the curvature of the connecting bar(s) and the separation or approach corrections of two vertebrae, but without making it difficult to engage a bar in the duct formed by the heads of the anchor members.

For achieving this goal, this equipment comprises:

at least one connecting bar having a length such that it is capable to span several vertebrae to be treated, at least one anchor member having an anchoring portion for anchoring on a vertebra be treated, of the “tulip” type, i.e., comprising a body and a head that forms an engagement duct for the connecting bar, this duct being closed, after placement of the connecting bar therein, by a stop member capable to be screwed on the head; the anchor member is of the so-called “polyaxial” type, i.e., with said head articulated relative to said body;

the head forms, on its side turned toward the body, outside said duct, an articulation portion including a completely or partially spherical surface, and forms thereon a distal bearing surface;

the body forms an articulation cavity for receiving said completely or partially spherical surface of the articulation portion, this articulation cavity being defined by a bearing wall outwardly having a partially spherical shape;

the anchor member includes a ring located between the distal bearing surface formed by the head and the bearing wall comprised by the body, this ring having a partially spherical recessed surface for bearing against said bearing wall and being angularly mobile relative to the head;

the ring and said bearing surface comprise inter-engagement means;

the ring has an axis and is pivotable relative to the head about this axis;

the head has an axis and the inter-engagement means, in a first angular position of the ring, have a first inter-engagement position in which the ring is placed in a first position along the axis of the head, in which play exists between the ring and said bearing wall, such that the head is movable, in an articulated manner, relative to the body; the inter-engagement means have, in a second angular position of the ring, a second inter-engagement position in which they position and maintain the ring in a second position along the axis of the head, in which said play is eliminated and the ring presses against said bearing wall, such that the head is made immobile, or substantially immobile, relative to the body; and the ring comprises movement means for its pivoting movement, located angularly away from the openings by which said engagement duct emerges outside the head, such that the ring can be pivoted, by these movement means, even when a connecting bar is placed in said engagement duct.

The anchor member of the equipment according to the invention thus makes it possible at will, by pivoting the ring, to allow the polyaxiality of the head relative to the body to exist or to eliminate this polyaxiality.

In practice, the anchor member is placed on a vertebra, then, the ring being in said first angular position allowing the polyaxiality, the bar is placed in said engagement duct. The polyaxiality of the head facilitates the placement of the bar in the engagement duct. The stop member is next placed on the head without tightening so that the anchor member is still capable to slide along the bar. The placement of the bar makes it possible to bring the vertebrae into a correction position, which is, however, slightly lessened by the polyaxial nature of the anchor member; the vertebrae are then brought into a desired complete correction position, then the ring is pivoted to said second angular position, eliminating the polyaxiality. A separation or approach of the anchor member and another adjacent anchor member can then be done if necessary, so as to correct the position of the two vertebrae in which these anchor members are implanted. Once this correction is done, the stop member is tightened so as to immobilize the anchor member relative to the bar in the obtained correction position.

During this separation or approach, the movement done on the anchor member is perfectly transmitted to the vertebrae due to the elimination of the polyaxiality of the head relative to the body of the anchor member.

In this way, the invention provides equipment resolving the drawbacks of the equipment according to the prior art, i.e., allowing perfect transmission to the vertebrae of the corrections imposed by the curvature of the connecting bar(s) and the separation or approach corrections of two vertebrae, but without making it difficult to engage a bar in the ducts formed by the heads of the anchor members.

For simplification of the description of the invention, it has been described above that the head comprises said articulation portion, the body comprises said bearing wall and the inter-engagement means are arranged on the ring and on said bearing surface comprised by the head. It must be understood that the invention encompasses the alternative embodiment consisting of inverting the arrangement of these means, i.e., the head would comprise said bearing wall, the body would comprise said articulation portion and a bearing surface, and the inter-engagement means would be arranged on the ring and on the bearing surface comprised by the body.

The method according to the invention comprises the following steps:

producing said articulation portion in two pieces, i.e., a lower axial slug secured to the head and an at least partially spherical part, intended to be fastened on said slug;

producing said bearing wall in the form of a separate part from the body of the anchor member;

engaging the ring and said bearing wall on said lower axial slug, then fastening said at least partially spherical part on said slug, so as to assemble the head, the ring, the bearing wall and this at least partially spherical part to one another; and fastening said bearing wall to the body of the anchor member.

This method therefore differs from a conventional method for manufacturing a polyaxial anchor member, as in particular described by the publication of the aforementioned patent application No. WO 98/55038; indeed, the conventional method consists of producing said bearing wall so as to be integral with the body of the anchor member and crimping this bearing wall around the at least partially spherical portion intended to be received in the cavity defined by this bearing wall, this at least partially spherical portion in turn being integral with the articulated part. In the method according to the invention, on the contrary, said articulation portion is in two parts, i.e., slug/partially spherical part, and said bearing wall is made separately from the body of the anchor member, such that the ring and the bearing wall can easily be assembled to the head.

The fastening of said bearing wall to the body of the anchor member can in particular be done using welding of the periphery of the edge of the bearing wall to the body of the anchor member.

According to one possible embodiment of the invention, the ring comprises two diametrically opposite extensions, intended to extend across from respective openings of the head by which said engagement duct emerges outside the head, these extensions being intended to receive the connecting bar engaged in this engagement duct and to transmit the tightening force exerted on the connecting bar by the stop member to the ring.

This tightening force thus completes the force exerted by said inter-engagement means on the articulation connecting the head to the body, or replaces that force. It makes it possible to ensure reliable blocking of the polyaxiality of the head over time, capable to perfectly withstand repeated stresses exerted on the equipment by the patient's movements.

Each extension could have a length (i.e., a dimension in the direction of the circumference of the ring) significantly smaller than the width (i.e., the dimension in the direction of the circumference of the head) of the corresponding opening of the head by which said engagement duct emerges outside the head, such that the extension would move inside this opening during pivoting of the ring between said first and second angular positions of the ring. Preferably, however, each extension has a length (i.e., a dimension in the direction of the circumference of the ring) smaller than the width (i.e., the dimension in the direction of the circumference of the head) of the corresponding opening of the head by which said engagement duct emerges outside the head; and the head comprises a slot for moving said extension during pivoting of the ring between said first and second angular positions of the ring, extending in the base of the head and being arranged past the edges of the head laterally defining said opening.

The extensions thus have significant lengths, allowing broad bearing of the connecting bar against them.

Preferably, each extension has a boss protruding from it, radially toward the inside of the ring, and the head forms a recess in the wall defining the corresponding groove in the radial direction, said boss being capable to be received in said recess in said first angular position, in order to give the ring pivoting stability in this position, said boss being capable to be forcibly removed from said recess during the pivoting of the ring toward said second angular position.

The reception of the boss in said recess makes it possible to give the ring a position stability in said first angular position, and therefore prevents any untimely pivoting of the ring toward said second position, which facilitates and secures the use of the equipment according to the invention.

Likewise, each extension can have a boss protruding from it, radially toward the inside of the ring, and the head can form a recess in the wall defining the corresponding slot in the radial direction, said boss being capable to be received in said recess in said second angular position of the ring, said boss being capable to be forcibly removed from said recess during the pivoting of the ring toward said first angular position.

This boss and this recess make it possible, in the same manner as before, to stabilize the ring in said second angular position, and consequently to secure the blocking of the polyaxiality allowed by this ring in this second angular position.

Preferably, each extension has, on its proximal edge, at least one bowed indentation intended to receive the connecting bar in one of said first and second angular positions.

The bar is thus received against the extensions by rounded surfaces, allowing wider contact zones.

Preferably, each extension has, on its proximal edge, two bowed indentations as mentioned above, adjacent to one another, one pair of indentations of the two extensions being intended to receive the connecting bar in said first angular position of the ring and the other pair of indentations being intended to receive the connecting bar in said second angular position of the ring.

Said inter-engagement means could be formed by ramps separating the ring and the head in said second angular position; preferably, however, these inter-engagement means are formed by studs protruding from one of the ring and said distal bearing surface formed by the head, and by cavities arranged in the other of said distal bearing surface and the ring, the studs being capable to be received in said cavities in said first angular position of the ring, and allowing the ring to be placed in said first position along the axis of the head, and being angularly offset relative to said cavities in said second angular position of this ring, and therefore making it possible to bring the ring into said second position along the axis of the head.

Preferably, the means for the pivoting movement of the ring are formed by diametrically opposite lugs, forming bearing engagement surfaces located on an axis perpendicular to the axis of the engagement duct, or forming a large angle with that axis of at least 45°, for the engagement of an instrument for maneuvering the ring.

The invention will be well understood, and other features and advantages thereof will appear, in reference to the appended diagrammatic drawing, showing, as a non-limiting examples, two possible embodiments of an anchor member comprised by the equipment in question.

DESCRIPTION OF THE PREFERRED EMBODIMENTS

Figure 1:
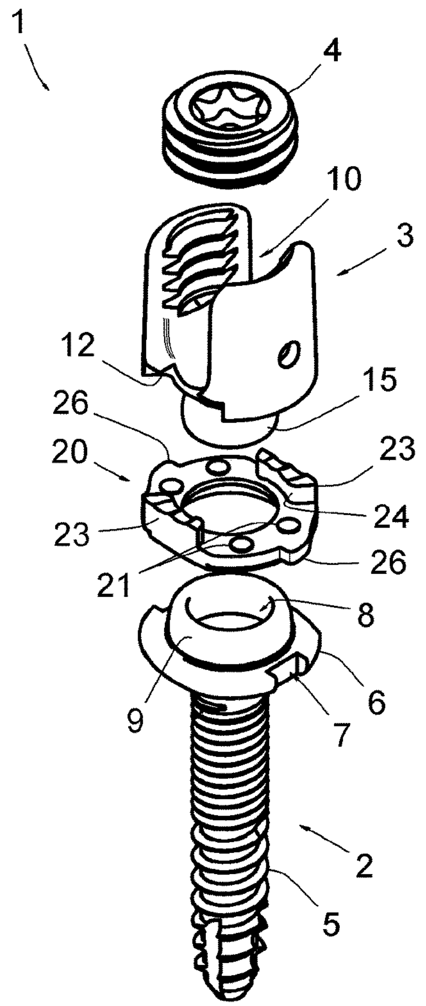
FIG. 1 is a view of this anchor member according to the first embodiment, in exploded perspective view from a first viewing angle.
Figure 2:
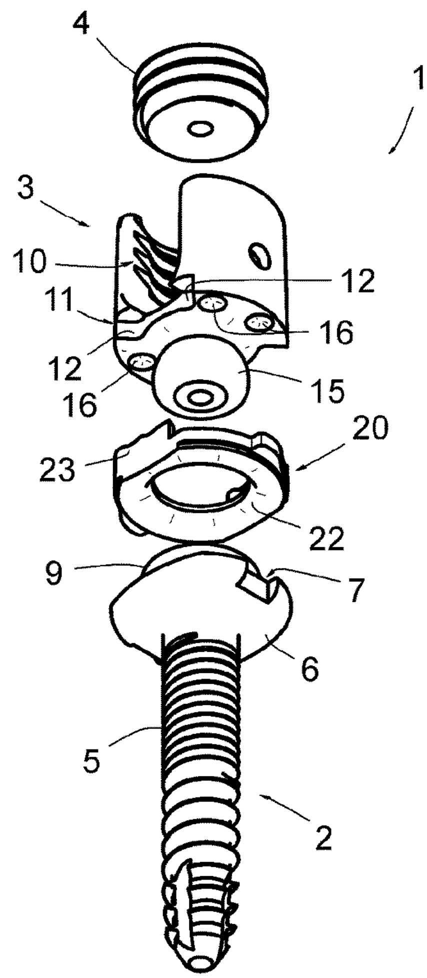
FIG. 2 is a view similar to FIG. 1, from another viewing angle.

FIGS. 1 and 2 show an anchor member 1 forming part of a vertebral osteosynthesis equipment. This equipment further comprises a plurality of anchor members 1, connecting bars (not shown) designed to connect several vertebrae be treated to one another, these bars being fixed to these vertebrae using anchor members 1.

The anchor member 1 is of the so-called "tulip" type, i.e., comprising a body 2, a widened head 3 and a set screw 4 capable to be screwed into the head 3.

In the illustrated example, the body 2 comprises a threaded part 5 allowing it to be screwed in the resected pedicle of a vertebra. At its proximal end, it has a collar 6 provided with notches 7 for rotational maneuvering during its screwing, and comprises a spherical articulation cavity 8 defined by a peripheral wall 9 coaxial to the body 2. This peripheral wall 9 is crimped on an articulation portion 15 comprised by the head 3, described later, this crimping assembling the head 3 to the body 2, with "polyaxiality", i.e., with articulation of the head 3 relative to the body 2. The wall 9 outwardly has a sphere portion shape.

The head 3 is inwardly hollow and has two diametrically opposite openings, such that it forms an engagement duct 10 for a connecting bar. At the base of each opening, the head 3 has a transverse slot 11, longer than the width of the opening and centered on the median axis of that opening. The slot 11 is defined, in the radial direction of the head 3, by a wall forming two recesses 12 at the ends of the slot 11.

The head 3 also comprises a distal axial portion 15, spherical or partially spherical, received in the cavity 8 and retained in said cavity by crimping of the wall 9 thereon, as mentioned above.

The head 3 further forms a substantially planar distal bearing face, in which the slots 11 emerge and which includes four cavities 16 with a rounded bottom.

Figure 3:
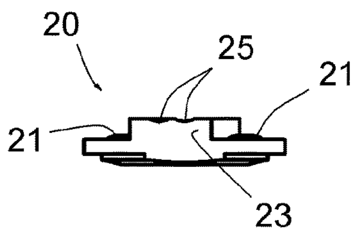
FIG. 3 is a side view of a ring comprised by this anchor member.
Figure 4:
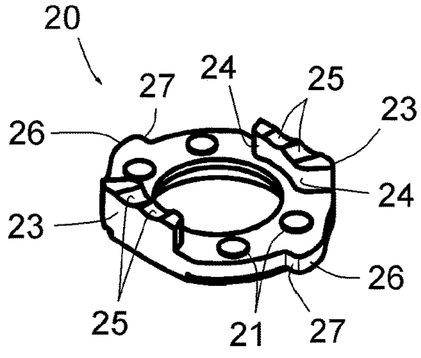
FIG. 4 is a perspective view of this ring, enlarged.
Figure 5:
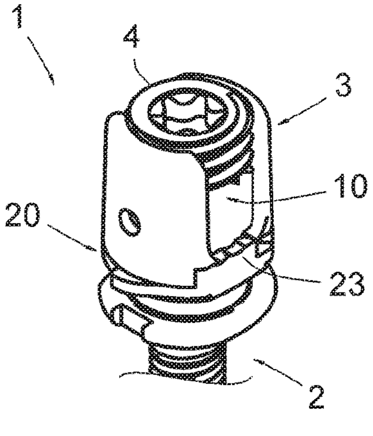
FIGS. 5, 7 and 9 are partial views of the anchor member in the assembled state, in perspective, side and top view, respectively, in a first angular position of said ring.
Figure 6:
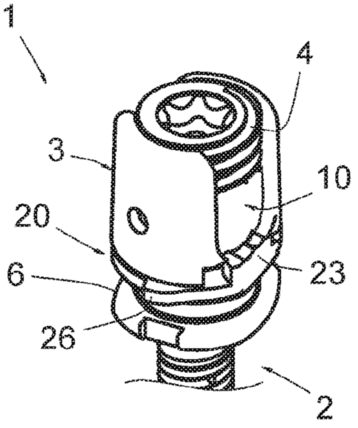
FIGS. 6, 8 and 10 are views of the anchor member respectively similar to FIGS. 5, 7 and 9, in a second angular position of said ring.
Figure 7:
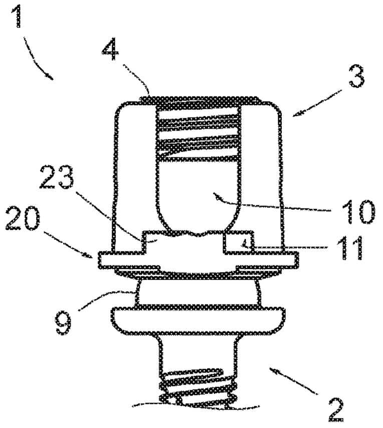
Figure 8:
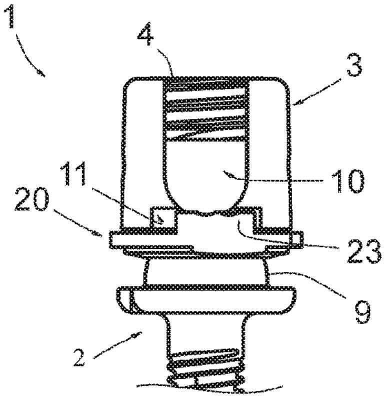

The anchor member 1 also comprises a ring 20, also visible, and more particularly, in FIGS. 3 and 4.

This ring 20 has a proximal face from which four bosses 21 protrude in the form of a spherical cap, sized so as to be able, in said first angular position of the ring 20, to be completely inserted in the cavities 16, and which are angularly offset from these cavities 16 in said second angular position.

The ring 20 also has a distal face 22 in the form of a recessed surface, capable to bear against the wall 9 with an articulated movement capacity.

The ring 20 also comprises, on its proximal side, two diametrically opposite studs 23, axially protruding from the proximal side of the ring 20, longer than they are tall (the length being the dimension of the studs 23 in the direction of the circumference of the head 3, and the height being their dimension in the direction of the axis of the head 3). These studs 23 are capable to be received in the slots 11 and to be moved in these slots when the ring 20 is maneuvered to pivot along its axis, both in the longitudinal direction of these slots 11 and in the axial direction of the anchor member 1. Each stud 23 has, at its longitudinal ends, two bosses 24 protruding toward the inside of the ring 20, and in its upper face, two indentations 25 capable to receive the connecting bar placed in the duct 10, in said first and second angular positions of the ring 20.

Figure 9:
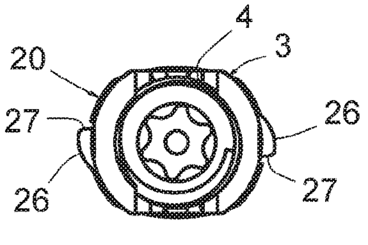
Figure 10:
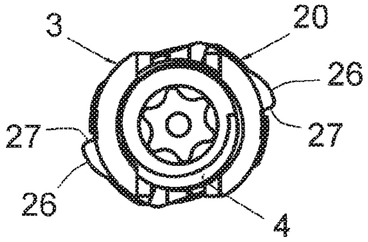
Figure 11:
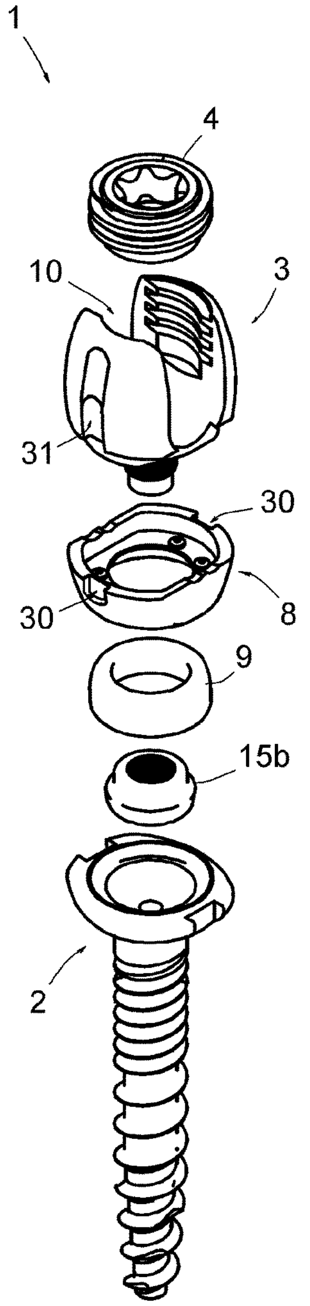
FIG. 11 is a view of the anchor member according to the second embodiment, in exploded perspective view.
Figure 12:
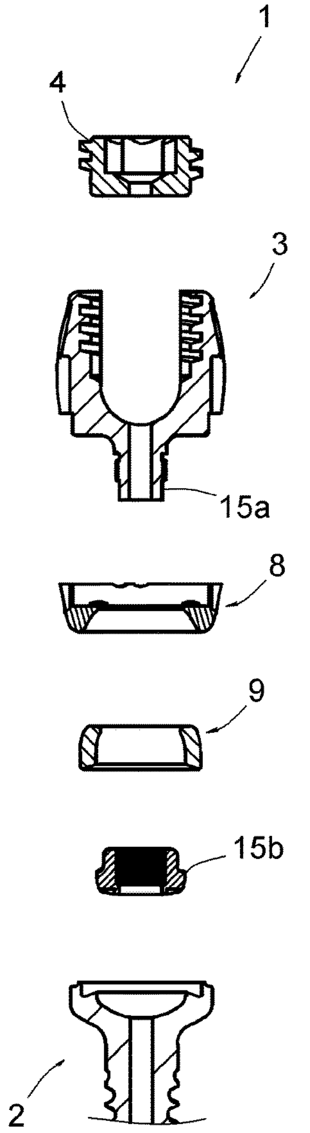
FIG. 12 is a longitudinal sectional side view passing through the axis of the anchor member.

The ring 20 further has two diametrically opposite lugs 26, protruding radially outwardly, which form two radial bearing surfaces 27 for receiving corresponding surfaces of an instrument (not shown) for maneuvering the ring 20 in view of pivoting this ring. These radial faces 27 are, in said first angular position of the ring 20, located in a plane substantially perpendicular to the plane passing through the middle of the studs 23, as shown in FIG. 9.

Said instrument for maneuvering the ring 20 is tubular so as to be capable to be engaged on the head 3 of an anchor member 1 and forms two radial surfaces engaged with the radial faces 27. It further includes diametrically opposite notches, perpendicular to these two radial surfaces, that have, in terms of width, a dimension much larger than the diameter of the bar, so as to allow said engagement of the instrument and surfaces 27 while a connecting bar is engaged in the duct 10 of the head 3 and so as to allow the actuation of the ring 20 to pivot between said first angular position and said second angular position.

In reference to FIGS. 5 to 10, it is understood that, in said first angular position (FIGS. 5, 7 and 9), as a result of the insertion of the bosses 21 in the cavities 16, the ring 20 is not pressed against the bearing wall 9 and play exists between this ring 20 and this bearing wall 9, allowing the polyaxial mobility of the head 3 relative to the body 2; however, in said second angular position (FIGS. 6, 8 and 10), as a result of the offset of the bosses 21 relative to the cavities 16, that these bosses axially separate the ring 20 from the head 3 and press said ring 20 against the wall 9, eliminating said play and making the head 3 immobile, or substantially immobile, relative to the body 2.

It will also be understood that the studs 23 move in the slots 11 during this pivoting and that both of the bosses 24, by their reception in the corresponding recesses 12, make it possible to give the ring 20 stability in each of said first and second angular positions. Furthermore, in one or the other of these angular positions, a pair of indentations 25 of the extensions is parallel to the axis of the duct 10, forming rounded surfaces for receiving the connecting bar, therefore allowing wider contact zones between the bar and the extensions 23.

The set screw 4 is of a known type, being outwardly threaded so as to be capable to be screwed to the inside of the head 3.

In practice, a series of anchor members 1 is placed on a series of vertebrae, with the rings 20 of these anchor members 1 in said first angular position, and without the set screws 4. After appropriate bending, the connecting bar is engaged in the different ducts 10 of these anchor members 1, this engagement being facilitated by the polyaxiality of the heads 3. The screws 4 are next placed on the heads 3 without tightening so as to allow the possibility of sliding of the anchor members 1 along the bar to remain. The placement of the bar makes it possible to bring the vertebrae into a correction position, which is, however, slightly lessened by the polyaxiality of the anchor members 1; the vertebrae are then brought into a desired complete correction position, then the rings 20 are pivoted in said second angular position, using said maneuvering instrument, eliminating the polyaxiality of the heads 3. A separation or approach of two adjacent anchor members 1 can be done if necessary, so as to correct the position of the two vertebrae in which these anchor members 1 are implanted. Once this correction is done, the screws 4 are tightened so as to immobilize the anchor members relative to the bar in the obtained correction position.

FIGS. 11 to 14 show the anchor member 1 according to the second embodiment and make it possible to illustrate a method for manufacturing this anchor member. For simplification reasons, the component elements already described and that are found identically or similarly in the second embodiment are designated using the same references.

In this case, the ring 8 has no extensions 23: the vertebral bar bears directly on this ring at portions thereof located below openings through which the duct 10 emerges outside the head 3. The ring 8 is also provided with no lugs 26 and instead comprises two indentations 30 allowing it to pivot relative to the head 3, using an appropriate instrument (not shown). This instrument comprises a tubular portion intended to be engaged on the head 3 and two inner lugs intended to be engaged in the indentations 30; to allow these inner lugs to cross the head 3 and be capable to be engaged in the indentations 30, the head 3 comprises two slots 31 capable to slidingly receive these lugs during the engagement of said instrument on the head 3.

FIGS. 11 to 14 show that the articulation portion comprises two parts 15*a*, 15*b*, i.e., a lower axial slug 15*a* secured to the head 3 and a partially spherical part 15*b*. The slug 15*a* has a thread and the part 15*b* has a tapped hole allowing it to be screwed on this thread, such that the part 15*b* can be fixed on this slug 15*a*.

It also appears that the bearing wall 9 is made as a part separated from the body 2.

Figure 13:
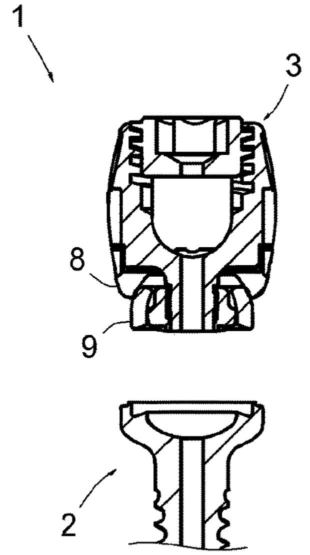
FIG. 13 is a view of the anchor member similar to FIG. 12, in a non-final assembled state.
Figure 14:
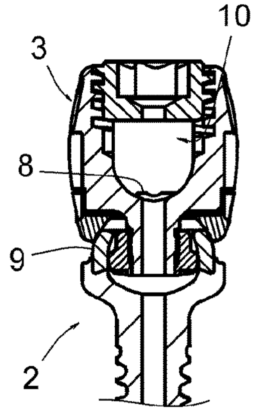
FIG. 14 is a view of the anchor member similar to FIG. 13, in the final assembly state.

As will be understood, this structure is designed to allow the assembly of the anchor member 1 according to the method comprising the following steps:

engaging the ring 8 and the bearing wall 9 on the slug 15*a*;

fastening the part 15*b* on this slug by screwing, so as to assemble the head 3, the ring 8, the bearing wall 9 and this part 15*b* to one another, as shown in FIG. 13; and fastening the bearing wall 9 to the body 2, in particular by welding of the periphery of the edge of this bearing wall to this body, as shown in FIG. 13.

In reference to FIGS. 1 and 2, it appears that the anchor member 1 according to the first embodiment is also made using the same method.

The invention thus provides a vertebral osteosynthesis equipment 1 having the decisive advantage of allowing perfect transmission to the vertebrae of the corrections imposed by the curvature of the connecting bar(s) and the separation or approach corrections of two vertebrae, but without making it difficult to engage a bar in the ducts 10 formed by the heads 3 of the anchor members 1.

What is claimed is:

1. A vertebral osteosynthesis equipment comprising:

at least one connecting bar having a length capable to span several vertebrae to be treated;

at least one anchor member having an anchoring portion for anchoring on a vertebra be treated, the at least one anchor including a body and a head that forms an engagement duct for the connecting bar, the engagement duct being intended to be closed, after placement of the connecting bar therein, by a threaded member capable to be screwed on the head; the anchor member is a "polyaxial" anchor member with said head articulated relative to said body;

the head forms, on a side turned toward the body, outside said duct, an articulation portion including a completely or partially spherical surface, and forms thereon a distal bearing surface;

the body forms an articulation cavity for receiving said completely or partially spherical surface of the articulation portion, the articulation cavity being defined by a bearing wall outwardly having a partially spherical shape;

the anchor member includes a ring located between the distal bearing surface formed by the head and the bearing wall comprised by the body, the ring having a partially spherical recessed surface for bearing against said bearing wall and being angularly mobile relative to the head;

the ring and said distal bearing surface comprise an inter-engagement device;

the ring has an axis and is pivotable relative to the head about this axis;

the head has an axis and the inter-engagement means, in a first angular position of the ring, have a first inter-engagement position in which the ring is placed in a first position along the axis of the head, in which play exists between the ring and said bearing wall, such that the head is movable, in an articulated manner, relative to the body; the inter-engagement device have, in a second angular position of the ring, a second inter-engagement position in which they position and maintain the ring in a second position along the axis of the head, in which said play is eliminated and the ring presses against said bearing wall, such that the head is made immobile, or substantially immobile, relative to the body; and the ring comprises a movement device for its pivoting movement, located angularly away from openings by which said engagement duct emerges outside the head, such that the ring can be pivoted, by the movement device, even when a connecting bar is placed in said engagement duct.

2. The vertebral osteosynthesis equipment according to claim 1, wherein the ring comprises two diametrically opposite extensions, intended to extend across from the respective openings of the head by which said engagement duct emerges outside the head, these extensions being intended to receive the connecting bar engaged in this engagement duct and to transmit to the ring the tightening force exerted on the connecting bar by the threaded member.

3. The vertebral osteosynthesis equipment according to claim 2, wherein:

each extension has a length smaller than a width of the corresponding opening of the head by which said engagement duct emerges outside the head; and the head comprises a slot for moving said extension during pivoting of the ring between said first and second angular positions of the ring, extending in a base of the head and being arranged past edges of the head laterally defining said opening.

4. The vertebral osteosynthesis equipment according to claim 2, wherein each extension has a boss protruding therefrom, radially toward the inside of the ring, and the head forms a recess defining a corresponding groove in a radial direction, said boss being capable to be received in said recess in said first angular position, in order to give the ring pivoting stability in the first angular position, said boss being capable to be forcibly removed from said recess during the pivoting of the ring toward said second angular position.

5. The vertebral osteosynthesis equipment according to claim 2, wherein each extension has a boss protruding therefrom, radially ward the inside f the ring, and the head forms a recess defining a corresponding slot in a radial direction, said boss being capable to be received in said recess in said second angular position of the ring, in order to give the ring pivoting stability in the second angular position, said boss being capable to be forcibly removed from said recess during the pivoting of the ring toward said first angular position.

6. The vertebral osteosynthesis equipment according to claim 2, wherein each extension has, on a proximal edge, at least one bowed indentation adapted to receive the connecting bar in one of said first and second angular positions.

7. The vertebral osteosynthesis equipment according to claim 6, wherein each extension has, on its proximal edge, two bowed indentations, adjacent to one another, one pair of indentations of the two extensions being adapted to receive the connecting bar in said first angular position of the ring and the other pair of indentations being adapted to receive the connecting bar in said second angular position of the ring.

8. The vertebral osteosynthesis equipment according to claim 1, wherein said inter-engagement device is formed by studs protruding from one of the ring and said distal bearing surface formed by the head, and by cavities arranged in the other of said distal bearing surface and the ring, the studs being capable to be received in said cavities in said first angular position of the ring, and allowing the ring to be placed in said first position along the axis of the head, and being angularly offset relative to said cavities in said second angular position of this ring, and therefore making it possible to bring the ring into said second position along the axis of the head.

9. The vertebral osteosynthesis equipment according to claim 1, wherein the movement device of the ring is formed by diametrically opposite lugs, forming bearing engagement surfaces located on an axis perpendicular to an axis of the engagement duct, or forming a large angle with that axis, of at least 45°, for the engagement of an instrument for maneuvering the ring.

10. A method for manufacturing an anchor member according to claim 1, wherein the method comprises the following steps:

producing said articulation portion in two pieces: a lower axial slug secured to the head and an at least partially spherical part, intended to be fastened on said slug;

producing said bearing wall in the form of a separate part from the body of the anchor member;

engaging the ring and said bearing wall on said lower axial slug, then fastening said at least partially spherical part on said slug, so as to assemble the head, the ring, the bearing wall and this at least partially spherical part to one another; and fastening said bearing wall to the body of the anchor member.

* * * * *